US010568924B2

(12) United States Patent
Green

(10) Patent No.: US 10,568,924 B2
(45) Date of Patent: Feb. 25, 2020

(54) METHODS FOR THE DEVELOPMENT OF ORTANIQUE PEEL POLYMETHOXYLATED FLAVONES EXTRACT POWDER FOR COMMERCIAL APPLICATIONS

(71) Applicant: The University of the West Indies, Kingston (JM)

(72) Inventor: Curtis O. Green, St. Catherine (JM)

(73) Assignee: University of The West Indies, Kingston (JM)

(*) Notice: Subject to any disclaimer, the term of this patent is extended or adjusted under 35 U.S.C. 154(b) by 719 days.

(21) Appl. No.: 14/531,681

(22) Filed: Nov. 3, 2014

(65) Prior Publication Data

US 2015/0125557 A1 May 7, 2015

Related U.S. Application Data

(60) Provisional application No. 61/900,010, filed on Nov. 5, 2013.

(51) Int. Cl.
*A61K 36/752* (2006.01)

(52) U.S. Cl.
CPC ........ *A61K 36/752* (2013.01); *A61K 2236/33* (2013.01)

(58) Field of Classification Search
None
See application file for complete search history.

(56) References Cited

U.S. PATENT DOCUMENTS

| 8,268,369 | B2 | 9/2012 | Green et al. | |
|---|---|---|---|---|
| 2007/0275106 | A1* | 11/2007 | Ho | A61K 31/352 424/736 |
| 2010/0015255 | A1* | 1/2010 | Green | A61K 31/352 424/736 |
| 2011/0124722 | A1* | 5/2011 | Green | A61K 31/352 514/456 |

OTHER PUBLICATIONS

Green et al. (2007) Biomed. Chrmatogr. 21: 48-54.*
Green et al. (2011) Basic and Applied Pathology 4: 71-77.*
Green et al. (2012) J. Appl. Biomed. 10: 91-101.*
Green et al. (2013) Food and Chemical Toxicology 51: 306-309.*
Li et al. (2006) Life Sciences 79: 365-373.*
Kurowska, E. M. and Manthey, J. A., "Hypolipidemic effects and absorption of citrus polymethoxylated flavones in hamsters with diet-induced hypercholesterolemia," J. Agric. Food Chem., vol. 52, No. 10, pp. 2879-2886 (May 19, 2004).
Xu, G. H., et al., "Minerals, Phenolic Compounds, and Antioxidant Capacity of Ctirus Peel Extract by Hot Water," Journal of Food Science, vol. 73, No. 1, pp. C11-C18 (Jan./Feb. 2008).
"Crystalline" and "crystal", definitions of. The New Oxford American Dictionary, Second Edition, May 19, 2005, p. 409.
Hancock et al., "Characteristics and Significance of the Amorphous State in Pharmaceutical Systems," Journal of Pharmaceutical Sciences, Jan. 1997, vol. 86, No. 1, 12 pages.

* cited by examiner

*Primary Examiner* — Russell G Fiebig
(74) *Attorney, Agent, or Firm* — Wilmer Cutler Pickering Hale and Dorr LLP

(57) ABSTRACT

The present invention relates generally to methods of extraction and processing of polymethoxylated flavone ("PMF") powder from Ortanique peels for commercial application.

11 Claims, 2 Drawing Sheets

METHODS FOR THE DEVELOPMENT OF ORTANIQUE PEEL POLYMETHOXYLATED FLAVONES EXTRACT POWDER FOR COMMERCIAL APPLICATIONS

CROSS REFERENCE TO RELATED APPLICATION

Priority is herewith claimed under 35 U.S.C. § 119 (e) from Provisional Patent Application 61/900,010, filed Nov. 5, 2013, which is incorporated by reference in its entirety.

FIELD OF THE INVENTION

The present invention relates generally to extraction and processing of polymethoxylated flavones ("PMF").

BACKGROUND

Hyperlipidemia occurs when the body is unable to control its pool of lipids to maintain levels within optimal physiological ranges. This condition usually results from a disordered regulatory system that disrupts the activity of the various proteins involved in lipid metabolic pathways, thus altering the balance between lipid biosynthesis and clearance. Familial hypercholesterolemia (FH) affects approximately 1 in 500 people (approximately 10 million worldwide) and the elevated serum cholesterol concentrations associated with it is responsible for more than 50% risk of fatal or non-fatal coronary heart disease by age 50 in men and at least 30% in women aged 60 and above. The prevalence of hypercholesterolemia in Jamaica is estimated at 31%. Hypercholesterolemia is implicated in many cardiovascular diseases affecting people worldwide and pose tremendous burden on the global healthcare system. In the last decade, cardiovascular disease (CVD) has become the leading cause of death across the Caribbean and accounted for 19% of deaths overall in 1995.

Citrus fruits have been known since antiquity to exhibit several beneficial effects in humans (Gorinstein et al. 2001). The traditional use of citrus in the treatment of cardiovascular diseases such as atherosclerosis, circulation dysfunction and high cholesterol is well documented (Oliver-Bever 1986; Rogar 2002). Over the past decade several studies have sought to elucidate the health-promoting principles in citrus fruits with the aim of utilizing them in ameliorating the metabolic defects that accompany several diseases and disorders such as cancer, diabetes and hypercholesterolemia. The major conventional drugs used to treat hypercholesterolemia include the statins (Lovastatin, Pravastatin, Simvastatin etc.) and Niacin (Nicotinic acid). Although these drugs are effective in lowering serum cholesterol levels, they result in several adverse effects. Statins for example result in gastrointestinal upset, muscle aches, and hepatic injury. Rarer problems are myopathy (defined as muscle pain with serum creatine kinase concentrations of more than 1000 Upper liter), rash, peripheral neuropathy, and insomnia. Niacin also results in adverse effects including flushing, abdominal pain, vomiting, headache, or elevated serum aminotransferase levels indicating liver damage.

Studies have shown that Ortanique peel polymethoxylated flavones extracts displayed potent hypolipidemic efficacy without the side effects of conventional hypolipidimic drugs (Green et al., 2011, Green et al., 2012). It is therefore conceivable that this extract can be used to develop a wide range of nutraceutic and pharmaceutical products with hypolipidemic efficacy. It is therefore necessary to develop a cost-effective and commercially viable method of extracting and producing the starting material for developing these products.

SUMMARY

Several studies have been done on Ortanique peel polymethoxylated flavones extract ($PMF^{ORT}$) which showed that it displayed potent hypolipidemic and antioxidant properties in animal model of hypercholesterolemia compared to the conventional hypolipidemic drug niacin. The potency of the extract is due to the unique composition of the most bioactive polymethoxylated flavones (PMFs) present in the peel extract. This product would not only have great benefits for the healthcare system but would also result in increased revenues for the citrus industry.

In one aspect of the invention, a cost-effective method of extracting commercial quantities of the polymethoxylated flavones from ortanique (or any suitable citrus source) and produce an end-product that is more suitable for manufacturing a wide range of nutraceutic and pharmaceutic products is described. In another aspect, a crystalline, free-flowing powder extract is provided that can be readily incorporated into a range of food, neutraceutical and pharmaceutical products.

In one aspect, a method for making a crystalline powdered extract comprising polymethoxylated flavones from citrus peel includes:
  (a) providing powdered citrus peel;
  (b) extracting polymethoxylated flavones from the powdered citrus peel to obtain a citrus peel extract, said citrus peel extract comprising a liquid component and a solid component;
  (c) separating the liquid component from the solid component of the citrus peel extract;
  (d) drying the liquid component in a centrifugal evaporator to produce an intermediate citrus extract;
  (e) washing with one or more nonpolar solvents to the intermediate citrus extract and drying in a centrifugal evaporator to remove the nonpolar solvents;
wherein a crystalline powdered citrus extract is obtained.

In one or more embodiments, the citrus peel includes ortanique peel.

In any of the preceding embodiments, the nonpolar solvent is selected from the group consisting of pentane, hexane, diethyl ether, ethyl acetate and cyclohexane.

In any of the preceding embodiments, the nonpolar solvent is hexane.

In any of the preceding embodiments, the intermediate citrus extract is cycled through step (e) two or more times.

In any of the preceding embodiments, a first nonpolar solvent used in a first cycle of step (e) and a second nonpolar solvent is used in a second cycled of step (e), and for example, the first nonpolar solvent is hexane and the second nonpolar solvent is ethyl acetate.

In any of the preceding embodiments, the polymethoxylated flavones are extracted from the powdered citrus peel using methanol.

In any of the preceding embodiments, the polymethoxylated flavones are extracted from the powdered citrus peel using hot water, and for example, the water is boiling water, or the water temperature is greater than 70° C., or greater than 80° C., or greater than 90° C., or greater than 95° C.

In one aspect, the invention includes a crystalline powdered ortanique extract produced by the herein described method.

In one aspect, a flour is provided including a crystalline powdered ortanique extract produced by the herein described method.

In one aspect, a spice composition is provided including one or spices; and a crystalline powdered ortanique extract produced by the herein described method.

In one aspect a food product is provided including one or more food ingredients; and a crystalline powdered ortanique extract produced by the herein described method.

In one aspect a pharmaceutical formulation is provided comprising (a) a pharmaceutically acceptable carrier or vehicle; and (b) an effective amount of a crystalline powdered ortanique extract produced by the herein described method.

BRIEF DESCRIPTION OF THE DRAWING

The invention is described with reference to the following figure, which is presented for purposes of illustration only and which is not intending to be limiting of the invention.

DETAILED DESCRIPTION

Figure 1:
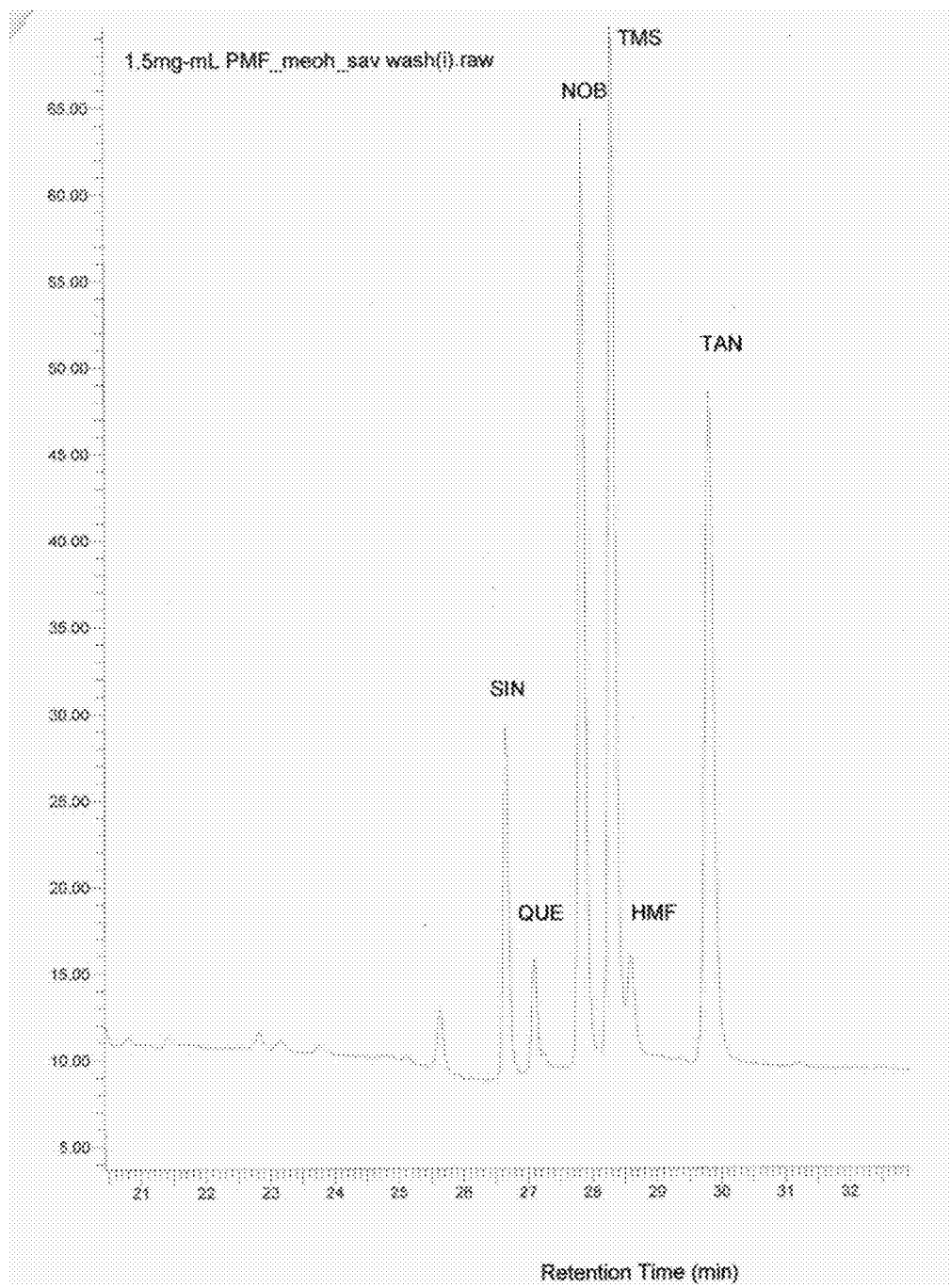
FIG. 1 is HPLC data showing the amounts of PMF in ortanique extract made using methanol extraction methods according to one or more embodiment.

A "polymethoxylated flavone" or "PMF" is a flavone substituted with methoxy groups, for example, with 2, 3, 4, 5, 6, 7 or 8 methoxy groups and optionally substituted with one or more hydroxy groups, for example, 1, 2 or 3 hydroxy groups. Polymethoxylated flavones are almost exclusively found in citrus fruits with a specific characteristic distribution for each variety. Illustrative polymethoxylated flavones include, but are not limited to: (a) 5,6,7,8,3',4'-hexamethoxyflavone (nobiletin); (b) 5,6,7,3',4'-pentamethoxyflavone (sinensetin); (c) 5,6,7,8,4'-pentamethoxyflavone (tangeretin); (d) 3,5,6,7,8,3',4'-heptamethoxyflavone (heptamethoxyflavone); (e) 3,5,7,8,3',4'-hexamethoxyflavone (hexamethyl-o-quercetagetin); (f) 5,6,7,4'-tetramethoxyflavone (tetramethylscutellarein); (g) 5-hydroxy-6,7,8,3',4'-pentamethoxyflavone; (h) 5,7,8,3',4'-pentamethoxyflavone; (i) 7-hydroxy-3,5,6,7,3',4'-hexamethoxyflavone; (j) 5-hydroxy-3,6,7,8,3',4'-hexamethoxyflavone; (k) 5,6,7,3',4',5'-hexamethoxyflavone; and (l) 5,7,3',4'-tetramethoxyflavone.

Two parameter values are "substantially similar" if they have values within ±10% of each other. The parameter values can be expressed as absolute values (e.g., weight) or as relative values (e.g., percentage).

As used herein, "about" means±10% of the value that follows it.

As used herein, "PMF-ORT" or $PMF^{ORT}$ is the Orthanique peel extract described herein.

As used herein, a solid is "soluble" in a given solvent if the solid has solubility of at least 0.1 g/L in the solvent under desired conditions, such as temperature, pressure, and pH.

Ortanique

The Ortanique fruit, a type of tangor, is a Jamaican hybrid between tangerine (*Citrus reticulata*) and sweet orange (*Citrus sinensis*). The name "Ortanique" is derived from a combination of the words "orange," "tangerine," and "unique" and is indigenous to Jamaica. Ortanique fruit is grown commercially in Jamaica. The Ortanique grows well in hot, dry weather on shallow bauxite soil at an elevation of about 2,500 feet. In Jamaica, Ortanique is cultivated on approximately 1550 acres and over 270,000 boxes of fresh fruits are produced annually, the majority of which (over 90%) is consumed locally.

The Ortanique peel contains a high percentage by weight of polymethoxylated flavones, and further contains a unique combination of six known polymethoxylated flavones, namely, nobiletin ("NOB"), sinensetin ("SIN"), tangeretin ("TAN"), heptamethoxyflavone ("HMF"), hexamethyl-o-quercetagetin ("QUE"), and tetramethylscutellarein ("TMS"). The Ortanique peel contains a higher overall percentage by weight of polymethoxylated flavones than either the tangerine peel or the sweet orange peel. Tangerine peel and sweet orange peel were previously reported to contain the highest percentage by weight of polymethoxylated flavones.

Compositions of Ortanique Peel Extract (PMF-ORT)

As has been previously noted, the distribution of particular polymethoxylated flavones in the Ortanique peel is unique, and is believed to have an important role in the potency of the Ortanique peel extract ($PMF^{ORT}$). See, United States Application Published Application 2010/0015255.

In some embodiments, the Ortanique peel extract contains over 40%, over 50%, over 60% or over 70% polymethoxylated flavones by weight. By weight, the Ortanique peel extract can contain about 15-21% nobiletin, about 14.5-20.5% tetramethylscutellarein, about 4-10% sinensetin, about 13-19% tangeretin, about 0.3-2.3% hexamethyl-o-quercetagetin, and about 0.5-3.5% heptamethoxyflavone. The values in this section refer to the percentages by weight of an extract that is typically about 60% PMFs, hence the percentages total ~60%.

In a specific embodiment, the Ortanique peel extract contains the following approximate weight percentages (w/w) of polymethoxylated flavones: 18% nobiletin, 17.5% tetramethylscutellarein, 7% sinensetin, 16% tangeretin, 1.3% hexamethyl-o-quercetagetin, and 2% heptamethoxyflavone. This distribution of polymethoxylated flavones is unique to the Ortanique peel, and is believed to have an important role in the potency of the Ortanique peel extract (PMF-ORT). Of course, the percentages of polymethoxylated flavones listed above can vary by as much as a few percent, e.g., up to 4%, from the values listed above.

Compositions described herein and extracts from the Ortanique peel can comprise substantially similar amounts of tetramethylscutellarein and nobiletin by weight. This amount can be, for example, 14-21%, 15-20%, 16-19%, or 17-18% for each of tetramethylscutellarein and nobiletin. In a specific embodiment, the composition comprises about 18% nobiletin and about 17.5% tetramethylscutellarein by weight.

In some embodiments, the composition comprises substantially similar amounts of tetramethylscutellarein, nobiletin, and tangeretin by weight. This amount can be 14-21%, 15-20%, 16-19% or 17-18% for each of tetramethylscutellarein, nobiletin, and tangeretin. In a specific embodiment, the composition comprises about 18% nobiletin, about 17.5% tetramethylscutellarein, and about 16% tangeretin by weight.

Method of Making Crystalline Citrus Peel Extract

Because only the peel of the Ortanique is used, $PMF^{ORT}$ can be made from Ortanique fruit that has been used for juice production. The juice production results in large quantities of the peel and other byproducts which end up being discarded and can even cause environmental problems. The methods disclosed herein allow for repurposing these discards of the juice industry.

The methods described herein can be generally used for extraction of polymethoxylated flavones from any citrus peel, such as those of mandarins (*Citrus reticulata*), sweet oranges (*Citrus sinensis*), *Citrus paradisi* (grapefruit) and *Citrus aurantium* L. (sour orange). The method is described below with reference to Ortanique fruit, a Jamaican hybrid between tangerine (*Citrus reticulata*) and sweet orange (*Citrus sinensis*); however, it can be readily used with any citrus source.

Current methods for extracting polymethoxylated flavones ("PMFs") from citrus peels are unsatisfactory. The PMFs are extracted from dried citrus byproduct and analyzed by reverse-phase HPLC and UV detection. The final product of extraction however is a semi-solid paste which is commercially unattractive as it is difficult for manufacturers to incorporate into nutraceutic and pharmaceutic products. The method of extraction is also expensive as it involved the use of large quantities of methanol which is a relatively expensive reagent.

In one aspect, the method includes heating citrus peels in hot water to extract polymethoxylated flavones. The supernatant liquid containing PMF extract can be separated from solids by centrifugation. The separated supernatant liquid is dried and washed with non-polar solvents using centrifugal evaporation, resulting in a crystalline product. While the preferred method uses hot water extraction, as is demonstrated herein below, the drying and purification method can be used with methanol extracts as well.

Hot water has been used to extract flavones from citrus peel See, Xu et al. "Mineral, Phenolic Compounds and Antioxidant Capacity of Citrus Peel Extract by Hot Water", J. Food Sci. Vol. 73, No. 1, pp. C11-C18 (2008). However, methods for production of high quality crystalline powdered extracts has not been investigated. Applicants have determined that the extraction of PMFs can be efficiently conducted using only water, e.g., without organic solvent. The extract yields are comparable to those conducted in methanol, however, the relative amounts of the various PMFs differs somewhat. The applicants have surprisingly discovered that use of a centrifugal evaporation, coupled with washing in non-polar solvents, provides a flowable crystalline powder without loss of yield. The crystalline powder is more easily integrated into existing manufacturing processes, making it an attractive format for use in foods, nutraceuticals and pharmaceuticals.

In some embodiments, the citrus peel and tissue can be dried and ground into a powder before extraction. For example, the fruits are peeled and the peel is dried. The peel can be dried using conventional methods. For example, the peel can be dried in an oven for a period of hours or days, or they can be air-dried, or sun-dried. The peels can be dried at a temperature in the range of 45-65° C. The dried peel is then milled into a fine powder. Milling the peel into a fine powder increases surface area for increased extraction of the compounds of interest.

In some embodiments, the dried powder is extracted from methanol. Methanol extraction can be carried out at room temperature for a period of for 24 or more hours, or for 48 or more hours, and for example up to 3-5 days. The extraction is effective in yielding the polymethoxylated flavones as demonstrated by the HPLC results noted herein below. See FIG. 1.

Figure 2:
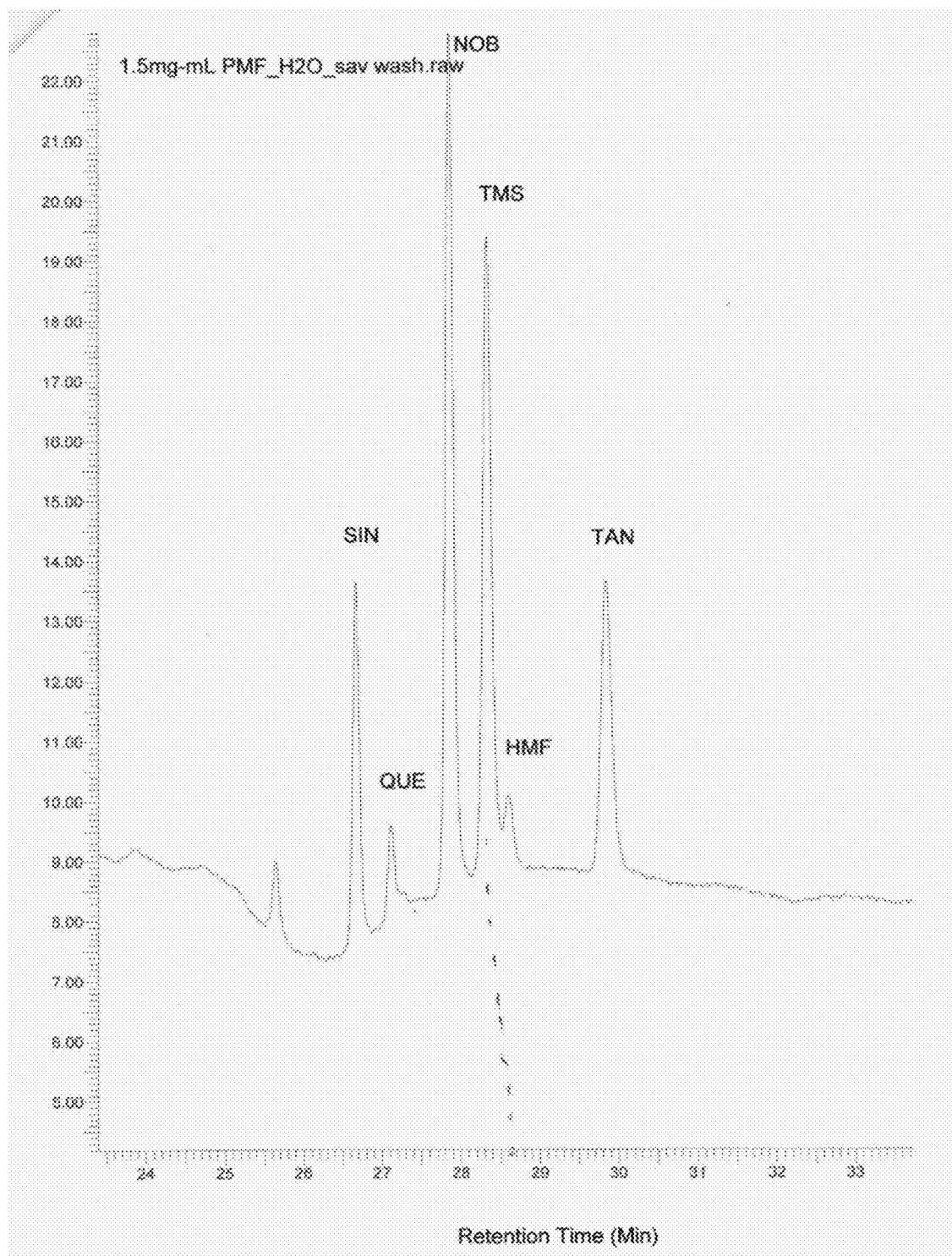
FIG. 2 is HPLC data showing the amounts of PMF in ortanique extract made using the hot water extraction methods disclosed herein.

In some embodiments, the dried powder is soaked in hot water to extract the polymethoxylated flavones. In certain embodiments, the water is at a temperature of greater than 80° C., or greater than 90° C. In other embodiments, the dried peels are heated in boiling water. The extraction can take place for several hours or several days, to obtain effectively full extraction of the polymethoxylated flavones. In certain embodiments, the citrus peels are boiled in water for 24 or more hours, or for 48 or more hours, and for example up to 3-5 days. The extraction is effective in yielding the polymethoxylated flavones as demonstrated by the HPLC results noted herein below. See, FIG. 2. The quantity of extract obtained is also comparable with methanol extract even though the duration of extraction was greater (though not significantly) for water extracts.

The methanol or hot water extraction mixture is then subjected to separation to remove the aqueous extract from the solid residue. The separation can be effected using any conventional method, such as gravity filtration, vacuum filtration and centrifugation. In one or more embodiments, the aqueous mixture is separated from the solid residue by centrifugation. Gravity and vacuum filtration methods can also be used but process is slow. Centrifugation is used for the water extract since it was difficult to filter the water extract using vacuum filtration as it contains oils which coat the filter paper used for filtration. The solids can be decanted off the supernatant and the supernatant can be collected and subjected to further centrifugation. Similarly, the solids can be resuspended and recentrifuged.

The supernatant is then dried to a solid. It surprisingly has been determined that use of a centrifugal vacuum concentrator provides an exceptionally high quality crystalline product. A centrifugal evaporator provides efficient and gentle evaporation of water from the extract. A centrifugal evaporator often comprises a vacuum pump connected to a centrifuge chamber in which the samples are placed. The system works by lowering the pressure in the centrifuge system—as the pressure drops so does the boiling point of the solvent(s) in the system. When the pressure is sufficiently low that the boiling points of the solvents are below the temperature of the sample holder, then they will boil. This enables solvent to be rapidly removed while the samples themselves are not heated to damaging temperatures. The centrifugal force generated by spinning the centrifuge rotor creates a pressure gradient within the solvent contained in the tubes or vials, this means that the samples boil from the top down, helping to prevent "bumping". Using smaller quantities of extract to solvent reduces the time taken to remove oils and other contaminants. The quantity of extract dried in a single sample can be increased provided that the area of the sample vials are increased to create a greater surface for contact with solvent.

After the extraction solvent is removed (water or methanol), the residue is further processed by centrifugal evaporation to remove residual impurities. In one or more embodiments, the residue is washed with a non-polar solvent to remove oil impurities that prevent crystallization and powder formation. Suitable non-polar solvents include pentane, hexane, diethyl ether, ethyl acetate and cyclohexane. Other solvents known in the art are contemplated, including but are not limited to ether, methyl tert-butyl ether, ethyl-isopropyl ether, higher ketones such as di-isopropyl ketone, dichloromethane, chloroform, carbon tetrachloride, other chlorinated solvents The dried residue is taken up in a suitable nonpolar solvent and then subjected to further rounds of centrifugal evaporation. In one or more embodiments, the dried residue is removed from the centrifugal evaporator, a non-polar solvent is added and the mixture is stirred, e.g., vortex, to provide effective mixing and contact. The mixture is then returned to the centrifugal evaporator to remove the nonpolar solvent. The extract residue can be subjected to one or two or three or four or more rounds of nonpolar washing.

In one or more embodiments, the powder is washed several times with hexane until oil impurities have been substantially removed. In this method using the evaporator there was clear evidence of oil removal as the liquid recovered with the hexane had visible oil droplets and strong aroma of citrus oils. The oils are sufficiently volatile to be removed with the hexane.

In other embodiments, the powder is washed with hexane, followed by washing with ethyl acetate. For example, hexane-washed residue is removed from the centrifugal evaporation and collected. The collected powders are then taken up in ethyl acetate and washed with ethyl acetate. The serial washing of the extract using hexanes and ethyl acetate is effective to remove oils, hexanes soluble contaminants and the drying of the sample at specific temperatures and pressure result in the formation of the powdered product with crystals.

The washed powder is then dried to obtain a freely flowing crystalline powder. At the end of the drying process there is little difference in appearance of the powders obtained from water or methanol extract; however, the HPLC profiles differ. The dried power is less bulky than the paste, has a clearer/cleaner appearance with visible crystals. It dissolves faster in solvents, has less oils, can be easily mixed with other powdered ingredients and can readily be stored and transferred from one container to the next without loss of material. It also has a lower liquid content which increases shelve life and reduces the possibility of microbial growth.

The benefits of centrifugal evaporation in obtaining a crystalline polymethoxylated flavone extract was not previously appreciated. As the instant application demonstrates, the drying of methanol or hot water extracts of citrus peel by centrifugal evaporation, that incorporates a series of washing steps using nonpolar solvents surprisingly produced a crystalline, free-flowing powder. In contrast, simple washing of the methanol extract using the same or similar sequence of nonpolar solvents resulted in an intractable paste. Also, freeze-drying of the water extract did not result in a powder.

Due to the high crystallinity and free flowing properties of the powder, the polymethoxylated flavone extract according to one or more embodiments can be used in a range of applications without requiring special handling that might be required for the paste that is obtained from methanol extraction. The polymethoxylated flavone extract according to one or more embodiments can be used as a potent hypocholesterolemic component of nutraceutic or pharmaceutical products. For example, the polymethoxylated flavone extract can be used in pharmaceutical products for treating hypercholesterolemia, or in nutraceutics for use by individuals with high cholesterol levels and/or for the health-conscious as well as diabetics desiring to keep their cholesterol levels low.

Methods of Using Ortanique Peel Extract

Methods for Treating Hypercholesterolemia

The Ortanique peel extract is useful for treatment or prevention of hypercholesterolemia. Experiments carried out on hypercholesterolemic rats indicated that the supplementation of the rats' diets with Ortanique peel extract resulted in statistically significant reductions in serum levels of total cholesterol and LDL cholesterol, as well as triglycerides, when compared to hypercholesterolemic rats fed normal food without supplementation and when compared to hypercholesterolemic rats fed food supplemented with niacin, a standard cholesterol reducing drug. The hypercholesterolemic rats fed Ortanique peel extract also experienced an elevation in serum HDL cholesterol levels compared to hypercholesterolemic rats fed normal food without supplementation and hypercholesterolemic rats fed food supplemented with niacin. This experimental data indicates that Ortanique peel extract is useful for reducing serum levels of total cholesterol in a subject, reducing serum levels of LDL cholesterol in a subject, reducing serum levels of triglycerides in a subject, and increasing serum levels of HDL cholesterol in a subject.

The Ortanique peel extract is more effective in treating hypercholesterolemia compared to peel extracts from other citrus fruits. For instance, a study performed using tangerine peel extract in hypercholesterolemic hamster diets resulted in significantly reduced serum total cholesterol and serum LDL cholesterol levels, and tended to reduce serum triacylglycerols, but resulted in no increase in serum HDL levels. By contrast, supplementation of diet with the Ortanique peel extract resulted in even greater reduction in total serum cholesterol, serum LDL cholesterol, and serum triglyceride levels, and further resulted in an increase in serum HDL levels. (See Kurowska and Manthey, Hypolipidemic Effects and Absorption of Citrus Polymethoxylated Flavones in Hamsters with Diet-Induced Hypercholesterolemia, *J. Agric. Food Chem.* 52: 2879-2886 (2004)).

Methods for Reducing LDL Cholesterol Levels

The Ortanique peel extract is useful for reducing LDL cholesterol levels in a subject in need thereof. Experiments carried out on hypercholesterolemic rats indicated that the supplementation of the rats' diets with Ortanique peel extract resulted in significant reductions in serum levels of LDL cholesterol compared to hypercholesterolemic rats fed normal food without supplementation and hypercholesterolemic rats fed food supplemented with niacin, a standard cholesterol reducing drug. This experimental data indicates that Ortanique peel extract is useful for reducing serum levels of LDL cholesterol in a subject.

Methods for Reducing Triglyceride Levels

The Ortanique peel extract is useful for reducing triglyceride levels in a subject in need thereof. Experiments carried out on hypercholesterolemic rats indicated that the supplementation of the rats' diets with Ortanique peel extract resulted in significant reductions in serum levels of triglycerides compared to hypercholesterolemic rats fed normal food without supplementation and hypercholesterolemic rats fed food supplemented with niacin, a standard cholesterol reducing drug. This experimental data indicates that Ortanique peel extract is useful for reducing serum levels of triglycerides in a subject.

Methods for Increasing HDL Cholesterol Levels

The Ortanique peel extract is useful for increasing HDL cholesterol levels in a subject in need thereof. Experiments carried out on hypercholesterolemic rats indicated that the supplementation of the rats' diets with Ortanique peel extract resulted in significant increases in serum levels of HDL cholesterol compared to hypercholesterolemic rats fed normal food without supplementation and hypercholesterolemic rats fed food supplemented with niacin, a standard cholesterol reducing drug. This experimental data indicates that Ortanique peel extract is useful for reducing serum levels of triglycerides in a subject.

Furthermore, with respect to HDL cholesterol levels, the Ortanique peel extract yields different, unexpected results when compared to peel extracts from other citrus fruits. For instance, a study performed using tangerine peel extract in hypercholesterolemic hamster diets resulted in no increase in serum HDL cholesterol levels. By contrast, the Ortanique peel extract study resulted in a significant increase in serum HDL cholesterol levels. (See Kurowska and Manthey, Hypolipidemic Effects and Absorption of Citrus Polymethoxylated Flavones in Hamsters with Diet-Induced Hypercholesterolemia, *J. Agric. Food Chem.* 52: 2879-2886 (2004)).

Further detail on compositions and methods for treating hypercholesterolemia, reducing LDL levels, increasing HDL levels and reducing triglyceride levels using Ortanique peel extract can be found in U.S. Pat. No. 8,268,369, which is incorporated in its entirety by reference.

Methods for Administering Peel Extract

The Ortanique peel extract can be administered to subjects in a variety of ways. In one embodiment, the Ortanique peel extract is administered orally to a subject, e.g., in the form of a tablet. The tablet can comprise Ortanique peel extract combined, in appropriate quantities, with a suitable medium to form a tablet. In another embodiment, the Ortanique peel extract is administered orally to a subject in the form of a capsule. The capsule can comprise Ortanique peel extract encapsulated in a standard ingestible capsule.

The polymethoxylated flavone extract according to one or more embodiments can also be used as a hypocholesterolemic agent can be component of pastries and other baked products. The product can also be incorporated into spices and cereals.

The Ortanique peel extract can also be incorporated into various foods and beverages, thus forming a nutraceutical. Examples of suitable beverages include, but are not limited to, fruit juices and sodas (e.g., colas). Examples of suitable foods include, but are not limited to, chocolates, snacks, confectionery, pizza, foods made from cereal flour (e.g., breads, cakes, crackers, cookies, biscuits, and noodles), and seasonings and spices used to prepare meat.

The Ortanique peel extract can be formulated into pharmaceutical compositions together with a pharmaceutically acceptable carrier or vehicle for oral administration in solid or liquid form, or for intravenous, intramuscular, or subcutaneous administration.

Pharmaceutically acceptable carriers for oral administration include capsules, tablets, pills, powders, troches, and granules. In the case of solid dosage forms, the pharmaceutically acceptable carrier can comprise at least one inert diluent such as sucrose, lactose or starch. Such pharmaceutically acceptable carriers can also comprise additional substances other than diluents, e.g., lubricating agents such as magnesium stearate. In the case of capsules, tablets, troches and pills, the pharmaceutically acceptable carrier can also comprise buffering agents. Carriers, such as tablets, pills and granules, can be prepared with enteric coatings on the surfaces of the tablets, pills or granules. Alternatively, the enteric coated compounds can be pressed into tablets, pills, or granules.

Pharmaceutically acceptable carriers include liquid dosage forms for oral administration, e.g., emulsions, solutions, suspensions, syrups and elixirs containing inert diluents commonly used in the art, such as water. Besides such inert diluents, compositions can also include adjuvants, such as wetting agents, emulsifying and suspending agents, and sweetening, flavoring agents.

Pharmaceutical compositions of the invention for parenteral administration comprise product according to the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Pharmaceutically acceptable carriers for intravenous administration include solutions containing pharmaceutically acceptable salts or sugars. Pharmaceutically acceptable carriers for intramuscular or subcutaneous injection include salts, oils, or sugars.

Furthermore, carriers such as solvents, water, buffers, alkanols, cyclodextrins and aralkanols can be used. Other auxiliary, non-toxic agents may be included, for example, polyethylene glycols or wetting agents.

The pharmaceutically acceptable carriers and compositions of the invention are formulated into unit dosage forms for administration to the patients. The dosage levels of active ingredient (i.e., Ortanique peel extract) in the unit dosage may be varied so as to obtain an amount of active ingredient that is effective to achieve a therapeutic effect in accordance with the desired method of administration. The selected dosage level therefore mainly depends upon the nature of the active ingredient, the route of administration, and the desired duration of treatment. If desired, the unit dosage can be such that the daily requirement for the Ortanique peel extract product is in one dose, or divided among multiple doses for administration, e.g., two, three, or four times per day.

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below. A number of references have been cited, the entire disclosures of which have been incorporated herein in their entirety.

Example 1. $PMF^{ORT}$ Powder from Methanol Extract

Mature Ortanique fruits were collected washed, peeled and the peels dried in an oven for 48 hours at 50° C. Dried peels were milled using a commercial blender. Reagent grade methanol was added to the powdered peel and infused for 48 hours. The methanol extract was filtered via vacuum filtration and the solvent removed by rotary evaporation. The extract was washed extensively with hexane, then ethyl acetate and placed in the oven at 55° C. for 6 hours. The resulting paste was dissolved in methanol and placed in vials which were then dried in a centrifugal vacuum separator, such as the Savant Speedvac concentrator from Thermoelectron.

An exemplary drying and purification cycle for the methanol extract is indicated below:

Step 1 Pressure 13 torr; Temperature 45° C.; time 2 hours

Step 2 Pressure 13 torr; Temperature 55° C.; time 2 hours

Each of the hexane washed and ethyl acetate washed samples were subjected to a similar cycle. Several cycles of washing with hexane and ethyl acetate were used. The resulting dried crystalline powdered product was then analyzed for PMF composition using HPLC. The crystalline powder is distinguishable from the paste as it is composed of fine divided powdered crystals as opposed a semi-solid paste.

Example 2. PMF$^{ORT}$ Powder from Hot Water Extract

The dried peels were obtained and used as described in Example 1.

Boiling distilled water was added to powdered peel and infused for 48 hours. The water extract was separated from solids by centrifugation. The infused peels were centrifuged for 15 minutes at a speed of 3000 rpm and the supernatants pooled. This was followed by drying in a Savant at 65° C. with several cycles of washing with hexane then ethyl acetate.

An exemplary drying and purification process for the water extract is indicated below:

Step 1 Pressure: 16 torr; heated for 1 hr; Temperature 65° C.; Time 2 hrs

Step 2 Pressure: 19.5 torr; heated for 1 hr; Temperature 70° C.; Time 3 hrs

Step 3 Pressure: 19.5 torr; heated for 1 hr; Temperature 75° C.; Time 3 hrs

All three were done initially however the last program Step 3 can be used for all samples. Several cycles of washing with hexane and ethyl acetate are involved. Each of the hexane washed and ethyl acetate washed samples were subjected to a similar cycle. The resulting dried crystalline powdered product was then analyzed for PMF composition using HPLC. The crystalline powder is distinguishable from the paste as it is composed of fine divided powdered crystals as opposed a semi-solid paste.

Comparative Example 1. Conventional Drying and Purification of Methanol Extract The dried peels were obtained and used as described in Example 1.

Methanol was added to powdered peel and infused for 48 hours. The methanol extract was filtered via vacuum filtration and the solvent removed by rotary evaporation. The extract was washed extensively with hexane, then ethyl acetate and placed in the oven at 55° C. for 6 hours. The resultant residue was a semi-solid paste.

Comparative Example 2. Freeze-Drying of Hot Water Extract

The dried peels were obtained and used as described in Example 1.

Boiling distilled water was added to powdered peel and infused for 48 hours. The water extract was separated from solids by centrifugation. The infused peels were centrifuged for 15 minutes at a speed of 3000 rpm and the supernatants pooled. The solvent was not removed as the temperature required (close to or greater than 100° C.) would affect the stability/integrity of the PMFs. Therefore the water extract was freeze dried without removal of solvent Freeze-drying works by freezing the material and then reducing the surrounding pressure to allow the frozen water in the material to sublimate directly from the solid phase to the gas phase. Freeze-frying did not form a crystalline solid. Upon removal of the sample from the freeze-dryer, the sample cake became a paste again.

Example 3. Comparison of Extract Properties

FIG. 1 as well as attached PMF profiles show that the methanol powder from Example 1 has a different composition from the paste from Comparative Example 1, as it contains more TMS compared to NOB. The water extract powder from Example 2 also has a slightly different composition from the methanol extract paste. Note that the values in the table total 100% and is a comparison of each PMF relative to each other. In contrast, PMF extract compositions reported hereinabove report the content of PMF relative to the entire extract, which contains other non-PMF components.

TABLE 1

Composition of PMFs in water and methanol extracts

| PMFs | Methanol extract paste (%) | Methanol extract powder (%) | Water extract powder (%) |
|---|---|---|---|
| SIN | 10.63 | 8.45 | 12.24 |
| QUE | 10.07 | 2.88 | 2.63 |
| NOB | 24.22 | 26.73 | 35.74 |
| TMS | 22.9 | 32.85 | 30.15 |
| HMF | 3.5 | 3.13 | 3.12 |
| TAN | 28.71 | 25.96 | 16.11 |

Overall the powder is a more commercially attractive alternative to the paste as it can be added easily to other powdered ingredients and has the potential for a wider range of applications. In addition the composition of the most potent PMFs (SIN, NOB, TAN, TMS) is enhanced thereby retaining its beneficially effects in vivo.

The invention claimed is:

1. A method for making a crystalline powdered extract comprising polymethoxylated flavones from citrus peel comprising:
   (a) providing a powdered citrus peel;
   (b) extracting polymethoxylated flavones from the powdered citrus peel using one or more extraction solvent(s) each selected from the group consisting of water and methanol to obtain a liquid component comprising the extraction solvent and a solid component;
   (c) separating the liquid component from the solid component;
   (d) removing the extraction solvent from the liquid component to produce an intermediate citrus extract residue;
   (e) washing the intermediate citrus extract residue with one or more nonpolar solvents each selected from the group consisting of: pentane, hexane, diethyl ether, ethyl acetate and cyclohexane; and
   (f) drying the washed intermediate citrus extract residue in a centrifugal evaporator to remove the nonpolar solvent(s) to produce the crystalline powdered citrus extract.

2. The method of claim 1, wherein the citrus peel comprises ortanique peel.

3. The method of claim 1, wherein the nonpolar solvent is hexane.

4. The method of claim 1, wherein the intermediate citrus extract residue is cycled through steps (e) and (f) two or more times.

5. The method of claim 4, wherein a first nonpolar solvent is used in a first cycle of steps (e) and (f) and a second nonpolar solvent is used in a second cycle of steps (e) and (f).

6. The method of claim 5, wherein the first nonpolar solvent is hexane and the second nonpolar solvent is ethyl acetate.

7. The method of claim 1, wherein the extraction solvent is boiling water.

8. The method of claim 1, wherein the extraction solvent is water, wherein the water temperature is greater than 70° C.

9. The method of claim 8, wherein the water temperature is greater than 80° C.

10. The method of claim 8, wherein the water temperature is greater than 90° C.

11. The method of claim 8, wherein the water temperature is greater than 95° C.

\* \* \* \* \*